(12) United States Patent
Li et al.

(10) Patent No.: US 8,513,472 B2
(45) Date of Patent: Aug. 20, 2013

(54) HIGH PURITY 1,6-HEXANEDIOL AND PROCESS FOR PREPARING THE SAME

(75) Inventors: Hirofumi Li, Ube (JP); Tomoyuki Itou, Ube (JP); Yoshiki Kawamura, Ube (JP); Toshiyuki Matsushita, Ube (JP)

(73) Assignee: Ube Industries, Ltd., Ube-Shi (JP)

( * ) Notice: Subject to any disclaimer, the term of this patent is extended or adjusted under 35 U.S.C. 154(b) by 240 days.

(21) Appl. No.: 13/124,973

(22) PCT Filed: Oct. 19, 2009

(86) PCT No.: PCT/JP2009/067973
§ 371 (c)(1),
(2), (4) Date: Apr. 19, 2011

(87) PCT Pub. No.: WO2010/047291
PCT Pub. Date: Apr. 29, 2010

(65) Prior Publication Data
US 2011/0201848 A1    Aug. 18, 2011

(30) Foreign Application Priority Data

Oct. 20, 2008  (JP) ................................. 2008-269488

(51) Int. Cl.
*C07C 27/04* (2006.01)
(52) U.S. Cl.
USPC ........... 568/884; 568/902; 568/903; 568/910; 568/913
(58) Field of Classification Search
None
See application file for complete search history.

(56) References Cited

U.S. PATENT DOCUMENTS

| 3,268,588 A | 8/1966 | Horlenko et al. |
| 6,008,418 A | 12/1999 | Baur et al. |
| 8,304,585 B2 * | 11/2012 | Ii et al. ........................ 568/884 |
| 2009/0048471 A1 | 2/2009 | Ii et al. |

FOREIGN PATENT DOCUMENTS

| JP | 3-115236 A | 5/1991 |
| JP | 2000-505468 A | 5/2000 |
| JP | 2001-316312 A | 11/2001 |
| JP | 2008-247742 A | 10/2008 |
| WO | WO 2007/080946 A1 | 7/2007 |

OTHER PUBLICATIONS

English Translation of International Preliminary Report on Patentability (Form PCT/Ib/373) and Written Opinion of the International Searching Authority (Form PCT/ISA/237) issued on May 17, 2011 in corresponding International Application PCT/JP2009/067973.
Notification of Transmittal of Translation of the International Preliminary Report on Patentability (Form PCT/IB/338), dated May 26, 2011, issued in corresponding International Application PCT/JP2009/067973.
Houben-Weyl, "Heterogen Katalysierte Hydrierungen", Methoden der Organischen Chemie, Band IV/Ic, Georg Thieme Verlag Stuttgart, 1980, pp. 16-26.
Houben-Weyl, "Homogen Katalysierte Hydrierungen", Methoden der Organischen Chemie, Band IV/Ic, Georg Thieme Verlag Stuttgart, 1980, pp. 45-67.
International Search Report for PCT/JP2009/067973, mailed on Dec. 22, 2009.
M. Larry Campbell, "Cyclohexane", Ullmann's Encyclopedia of Industrial Chemistry, 5th Ed, 1987, vol. A8, pp. 209-215.

* cited by examiner

*Primary Examiner* — Sudhakar Katakam
(74) *Attorney, Agent, or Firm* — Birch, Stewart, Kolasch & Birch, LLP (57) ABSTRACT

There is provided a process for preparing 1,6-hexanediol by esterifying a carboxylic acid mixture resulted from oxidation of cyclohexane with oxygen, and then hydrogenating the esters, which substantially does not contain a compound leading to a high ester value.
A process for preparing 1,6-hexanediol from a carboxylic acid mixture containing adipic acid and 6-hydroxycaproic acid, the carboxylic acid mixture is obtained as a by-product in oxidization of cyclohexane to cyclohexanone/cyclohexanol using oxygen or an oxygen-containing gas, the process comprises esterifying the acids with an alcohol, followed by hydrogenation, and the process is characterized by comprising the following steps of:
a) separating a component having a boiling point lower than that of water and the alcohol used in the esterification from a mixture obtained by the hydrogenation in a first distillation step;
b) separating an EV component having a boiling point higher than that of 1,6-hexanediol further in a second distillation step;
c) separating an EV component having a boiling point lower than that of 1,6-hexanediol further in a third distillation step; and then
d) obtaining 1,6-hexanediol in a fourth distillation step, in this order.

4 Claims, 2 Drawing Sheets

HIGH PURITY 1,6-HEXANEDIOL AND PROCESS FOR PREPARING THE SAME

TECHNICAL FIELD

The present invention relates to high purity 1,6-hexanediol and a process for preparing the same.

BACKGROUND ART

Conventionally, 1,6-hexanediol has been prepared by preparing a carboxylic acid mixture containing glutaric acid, adipic acid and 6-hydroxycaproic acid, which is obtained as a by-product in oxidation of cyclohexane to cyclohexanone and/or cyclohexanol with oxygen; esterifying the carboxylic acid mixture; and then hydrogenating the esters to prepare 1,6-hexanediol, which is further separated by distillation (Patent Document 1).

However, 1,6-hexanediol obtained by this preparation process involves the problems that it contains an esterified product extremely difficult to be separated by common distillation and therefore has a higher ester value (EV), disadvantageously. Further, the following problems are involved in 1,6-hexanediol obtained by this preparation process. For example, the polymerization rate is low and the resulting molecular weight is not sufficiently high when polycarbonate diol prepared from the aforementioned 1,6-hexanediol is subjected to urethanation. The same problems occur when the 1,6-hexanediol is used for urethanation as-is as a chain extender (Patent Document 2).

A process for preparing high purity 1,6-hexanediol is also known in which 1,4-dihydroxycyclohexane is removed as an impurity by esterifying a carboxylic acid mixture obtained by oxidation of cyclohexane with oxygen, and purifying the esters by distillation (Patent Document 3). However, ε-caprolactone or 6-hydroxycaproic acid ester is hardly removed by this purification process, because it shows irregular behavior that cannot be expected from vapor pressure in the purification step by distillation.

It is also known that ε-caprolactone or 6-hydroxycaproic acid ester present in a 1,6-hexanediol mixture obtained by hydrogenation of an esterified product can be separated by saponifying with caustic soda and then purifying by distillation (Patent Document 4). However, the bottom residue containing 1,6-hexanediol in the distillation after the saponification is solidified or becomes more viscous, and is difficult to be recycled for distillation or the like, and finally causes a reduction in efficiency of preparation of 1,6-hexanediol.
Patent Document 1: U.S. Pat. No. 3,268,588
Patent Document 2: Japanese Unexamined Patent Publication No. 2001-316312
Patent Document 3: Japanese Unexamined International Publication No. 2000-505468
Patent Document 4: Japanese Unexamined Patent Publication No. 1103-115236
Non-Patent Document 1: Ullmann's Encyclopedia of Industrial Chemistry, 5. Ed, 1987. Vol. A8, S. 2/9
Non-Patent Document 2: Houben-Weyl, Methoden der Organischen Chemie, Band IV/Ic, Georg Thieme Verlag Stuttgart, 1980. S. 4567
Non-Patent Document 3: Houben-Weyl, Methoden der Organischen Chemie, Band IV/1c, S. 16-26

DISCLOSURE OF THE INVENTION

Problems to be Solved by the Invention

An object of the present invention is to provide a process for preparing 1,6-hexanediol by esterifying a carboxylic acid mixture resulting from oxidation of cyclohexane with oxygen, and then hydrogenating the esters, in which high purity 1,6-hexanediol can be obtained in a high yield by reducing the amount of an esterified product of ε-caprolactone, 6-hydroxycaproic acid ester or the like leading to a high ester value (EV) in a purification step thereof.

As a result of extensive studies to overcome the above problems, the present inventors have found the following facts.

First, the inventors have found that it is difficult to remove ε-caprolactone or 6-hydroxycaproic acid ester in common distillation and that even further purification of 1,5-pentanediol and/or 1,6-hexanediol by distillation causes polymerization of 1,5-pentanediol and/or 1,6-hexanediol during distillation which generates a dimer ester [examples of which include an esterified product of 6-hydroxycaproic acid ester (or ε-caprolactone) with 1,6-hexanediol (i.e. 6-hydroxyhexyl 6-hydroxycaproate) or an ester compound of 6-hydroxycaproic acid ester (or ε-caprolactone) with 1,5-hexanediol (i.e. 5-hydroxypentyl 6-hydroxycaproate)]. This results in a loss of 1,6-hexanediol that is the objective compound. The inventors have also found that the generated dimer ester easily generates ε-caprolactone due to cyclization and elimination at terminal moieties of the dimer ester by heating. In this manner, the present inventors have revealed the behavior during distillation of ε-caprolactone or 6-hydroxycaproic acid ester present as a compound that cannot be sufficiently removed by common distillation.

The inventors have further found that polymerization of ε-caprolactone or 6-hydroxycaproic acid ester with 1,6-hexanediol or the like and terminal cyclization and elimination of the dimer ester occur more easily as the temperature is higher (e.g. 150° C. or higher).

The present inventors have completed the present invention based on the aforementioned findings.

Specifically, the present invention relates to the following:

1. A process for preparing 1,6-hexanediol from a carboxylic acid mixture containing adipic acid and 6-hydroxycaproic acid, the carboxylic acid mixture is obtained as a by-product in oxidization of cyclohexane to cyclohexanone/cyclohexanol using oxygen or an oxygen-containing gas, the process comprises esterifying these acids with an alcohol, followed by hydrogenation, and the process is characterized by comprising the following steps of:
    a) separating a component having a boiling point lower than that of water and the alcohol used in the esterification from a mixture obtained by the hydrogenation in a first distillation step;
    b) separating an EV component having a boiling point higher than that of 1,6-hexanediol further in a second distillation step;
    c) separating an EV component having a boiling point lower than that of 1,6-hexanediol further in a third distillation step; and
    d) obtaining 1,6-hexanediol in a fourth distillation step, in this order.

2. The process for preparing 1,6-hexanediol according to item 1 above, wherein the mixture obtained by the hydrogenation which is then subjected to the first distillation step is obtained by
    1) oxidizing cyclohexane to cyclohexanone/cyclohexanol using oxygen or an oxygen-containing gas and obtaining a carboxylic acid mixture containing adipic acid and 6-hydroxycaproic acid by extraction from a reaction mixture with water;
    2) treating the carboxylic acid mixture with an aliphatic alcohol having 1 to 4 carbon atoms to esterify mono- and dicarboxylic acids in the carboxylic acid mixture to obtain a mixture containing carboxylic acid esters;
3) separating a component having a boiling point lower than that of water and an excess of the alcohol from the mixture containing carboxylic acid esters by distillation;
4) distilling a bottom liquid after the separation by distillation to obtain the carboxylic acid esters; and then
5) hydrogenating the resulting carboxylic acid esters.

3. The process for preparing 1,6-hexanediol according to item 1 or 2 above, wherein the EV component having a boiling point higher than that of 1,6-hexanediol, which is separated in the second distillation step, is hydrogenated and introduced into the first distillation step.

4. 1,6-Hexanediol obtained by the preparation process according to any one of items 1 to 3 above.

5. 1,6-Hexanediol characterized in that it has an ester value (EV) of 1 mg KOH/g or less.

The EV component in the present specification refers to a lactone(s) such as γ-butyrolactone, δ-valerolactone or ε-caprolactone and an ester(s) such as dimethyl succinate, dimethyl glutarate, dimethyl adipate, methyl 4-hydroxybutylate, methyl 5-hydroxyvalerate, methyl 6-hydroxycaproate, a dimer ester of the lactone or ester and a dimer ester derived from the lactone or ester and an alcohol such as 1,5-pentanediol or 1,6-hexanediol. The ester value (EV) herein refers to a content of a lactone(s) such as γ-butyrolactone, 6-valerolactone or ε-caprolactone and an ester(s) such as dimethyl succinate, dimethyl glutarate, dimethyl adipate, methyl 4-hydroxybutylate, methyl 5-hydroxyvalerate, methyl 6-hydroxycaproate, a dimer ester of the lactone or ester and a dimer ester derived from the lactone or ester and an alcohol such as 1,5-pentanediol or 1,6-hexanediol. The ester value (EV) can be calculated by measuring the saponification value (SV) and the acid value (AV) and subtracting the acid value (AV) from the saponification value (SV), as described in JIS K0070-1992.

In the preparation process of the present invention, a high-boiling EV component including a dimer ester is separated from 1,6-hexanediol in the second distillation step. The second distillation step (column bottom residence time: generally 10 Hr or less) is generally carried out at a bottom liquid temperature of more than 150° C. (the step is inefficiently carried out at 150° C. or less because a large amount of 1,6-hexanediol is distilled off from the bottom liquid), and a considerable amount of ε-caprolactone is generated by terminal cyclization and elimination of the dimer ester. However, the present inventors have found that when a low-boiling EV component including ε-caprolactone or 6-hydroxycaproic acid ester is separated in the third distillation step (column bottom residence time: generally within 2 Hr) following the second distillation step [for example, by distillation at a temperature that does not substantially cause their polymerization (e.g. a column top temperature of 150° C. or less)], high purity 1,6-hexanediol can be obtained in a high yield by reducing the amount of ε-caprolactone or 6-hydroxycaproic acid ester substantially leading to a high ester value (EV) in the fourth distillation step.

When the order of distillation columns is reversed and a low-boiling EV component such as ε-caprolactone is first separated and removed, a low-boiling EV component such as ε-caprolactone is generated again by cyclization and elimination or the like during separation of a high-boiling EV component in the subsequent distillation column, making it impossible to obtain 1,6-hexanediol having a low ester value (EV). In contrast, 1,6-hexanediol having a low ester value (EV) can surprisingly be obtained by separating EV components in distillation columns in the order according to the present invention, that is, by separating a high-boiling EV component such as a dimer ester in a second distillation step and then separating a low-boiling EV component such as s-caprolactone in a third distillation step; this is an important feature of the present invention.

The preparation process of the present invention can easily remove without saponification with caustic soda EV components that are difficult to be separated only by distillation due to irregular behavior that cannot be expected from vapor pressure (e.g. δ-valerolactone, ε-caprolactone, methyl 6-hydroxycaproate, 6-hydroxyhexyl 6-hydroxycaproate and 5-hydroxypentyl 6-hydroxycaproate), and can produce high purity 1,6-hexanediol which has an ester value (EV) reduced to 1 mg KOH/g or less, indicating that it is substantially free from an esterified product of ε-caprolactone, 6-hydroxycaproic acid ester or the like.

The preparation process of the present invention can produce high purity 1,6-hexanediol in a high yield by hydrogenating and introducing into the first distillation step an EV component having a boiling point higher than that of 1,6-hexanediol (e.g. 6-hydroxyhexyl 6-hydroxycaproate or 5-hydroxypentyl 6-hydroxycaproate), which is separated in the second distillation step.

BEST MODE FOR CARRYING OUT THE INVENTION

The present invention relates to a process for preparing 1,6-hexanediol from a carboxylic acid mixture containing adipic acid and 6-hydroxycaproic acid, the carboxylic acid mixture is obtained as a by-product in oxidization of cyclohexane to cyclohexanone/cyclohexanol using oxygen or an oxygen-containing gas, the process comprises esterifying these acids with an alcohol, followed by hydrogenation, and the process is characterized by comprising the following steps of:
a) separating a component having a boiling point lower than that of water and the alcohol used in the esterification from a mixture obtained by the hydrogenation in a first distillation step;
b) separating an EV component having a boiling point higher than that of 1,6-hexanediol further in a second distillation step;
c) separating an EV component having a boiling point lower than that of 1,6-hexanediol further in a third distillation step; and
d) obtaining 1,6-hexanediol in a fourth distillation step, in this order.

The preparation process of the present invention will be described in detail below.
[Steps of Oxidation of Cyclohexane, Extraction with Water and Concentration]

A carboxylic acid mixture that is a raw material of the present invention can be an extract of a by-product of cyclohexanone/cyclohexanol obtained by oxidizing cyclohexane with oxygen or an oxygen-containing gas with water or an organic solvent. A carboxylic acid mixture can be an extract prepared as follows: extracting the by-product with alkali and neutralizing the resulting solution, combining the generated aqueous layer and an extract of the remaining organic layer with an aqueous inorganic salt solution, and re-extracting the aqueous layers with an organic solvent.

Here, the carboxylic acid mixture may be mentioned a mixture of carboxylic acids such as glutaric acid, adipic acid and 6-hydroxycaproic acid.

Examples of the method for oxidizing cyclohexane with oxygen or an oxygen-containing gas include a method described in Non-Patent Document 1. Specific examples include a method of introducing oxygen or an oxygen-containing gas into a reaction vessel in which cyclohexane and a salt of a metal such as cobalt (e.g. cobalt octylate) as a catalyst are placed, and reacting them at a temperature of 150 to 180° C. under a pressure of 0.8 to 1.2 MPa.

A carboxylic acid mixture that is a raw material of the present invention can be obtained by the following two methods, for example.

(First Method)

A carboxylic acid mixture is extracted with water from an oxidation mixture obtained by oxidizing cyclohexane with oxygen or an oxygen-containing gas as described above. Here, the amount of water is generally 1 to 10 wt % based on the oxidation mixture.

The extracted aqueous layer generally contains 1 to 4 wt % of adipic acid, 1 to 4 wt % of 6-hydroxycaproic acid, 0.1 to 1 wt % of glutaric acid, 0.1 to 1 wt % of 5-hydroxyvaleric acid, 0.1 to 0.5 wt % of 1,2-cyclohexanediol (cis and trans), 0.1 to 0.5 wt % of 1,4-cyclohexanediol (cis and trans), 0.2 to 1 wt % of formic acid and other various mono- and dicarboxylic acids, esters and oxo and oxa compounds. The content of each of the other mono- and dicarboxylic acids, esters and oxo and oxa compounds is generally not more than 0.5 wt %. Examples thereof include acetic acid, propionic acid, butyric acid, valeric acid, caproic acid, oxalic acid, malonic acid, succinic acid, 4-hydroxybutyric acid and γ-butyrolactone.

Then, the aqueous layer containing the carboxylic acid mixture is concentrated. The concentration is generally carried out by distillation. The aqueous layer is concentrated to ⅟50 to ½ time, and preferably ⅟20 to ⅓ time the weight of the aqueous layer before the concentration by distillation at a temperature of 10 to 250° C., preferably 20 to 200° C., and more preferably 30 to 200° C. under a pressure of 0.1 to 150 KPa, preferably 0.5 to 110 KPa, and more preferably 2 to 100 KPa. In this manner, water can be reduced to 2 wt % or less, and preferably 1 wt % or less based on the total amount.

(Second Method)

The oxidation mixture obtained by oxidizing cyclohexane with oxygen or an oxygen-containing gas as described above is saponified and the resulting alkaline solution is neutralized to separate an aqueous layer and an organic layer. The organic layer is extracted with an aqueous inorganic salt solution and the extract is combined with the aforementioned aqueous layer, followed by extraction with an organic solvent. An aqueous solution of an alkali metal hydroxide such as sodium hydroxide is used as an alkali for saponification. The concentration of the aqueous alkali metal hydroxide solution is generally 5 to 40 wt %, and the amount of the aqueous solution used is generally 1 to 2 moles per mole of the acids.

The resulting alkaline solution generally contains salts of various mono- and dicarboxylic acids such as adipic acid, 6-hydroxycaproic acid, glutaric acid, 5-hydroxyvaleric acid, formic acid, acetic acid, propionic acid, butyric acid, valeric acid, caproic acid, oxalic acid, malonic acid, succinic acid and 4-hydroxybutyric acid, and γ-butyrolactone, 1,2-cyclohexanediol (cis and trans), 1,4-cyclohexanediol (cis and trans) and the like.

The alkaline solution is neutralized with mineral acid (e.g. sulfuric acid) to pH 3 or less, and more preferably pH 2.5 or less. The aqueous layer and the organic layer can be separated by concentrating the alkaline solution previously or adjusting the concentration of mineral acid added so that the concentration of the inorganic salt in the aqueous layer at this time is 15 wt % or more, and preferably 20 wt % or more.

The aqueous layer mainly contains adipic acid, 6-hydroxycaproic acid and their oligomers. When the inorganic salt concentration in the aqueous layer is 15 wt % or less, the aqueous layer tends to contain an increased amount of monobasic acids which cannot be effective components of the objective 1,6-hexanediol.

The organic layer also contains adipic acid, 6-hydroxycaproic acid and their oligomers which are extracted with an aqueous inorganic salt solution having an inorganic salt concentration of 15 wt % or more, and more preferably 20 wt % or more. Examples of the aqueous inorganic salt solution include an aqueous sodium sulfate solution. The amount of the aqueous inorganic salt solution used is 1 to 10 times the amount of the organic layer on a volume basis.

The aforementioned aqueous layer is combined with the extract of the organic layer with the aqueous inorganic salt solution, followed by extraction with an organic solvent such as methyl isobutyl ketone. The amount of the organic solvent used is ⅟10 to 2 times the amount of the mixture in which the aqueous layer is combined with the extract of the organic layer with the aqueous inorganic salt solution on a volume basis.

The extracted organic layer generally contains 2 to 10 wt % of adipic acid, 2 to 10 wt % of 6-hydroxycaproic acid, 0.1 to 2 wt % of glutaric acid, 0.1 to 2 wt % of 5-hydroxyvaleric acid, 0.1 to 1 wt % of 1,2-cyclohexanediol (cis and trans), 0.1 to 1 wt % of 1,4-cyclohexanediol (cis and trans), 0.2 to 2 wt % of formic acid and other various mono- and dicarboxylic acids, esters and oxo and oxa compounds. The content of each of the other mono- and dicarboxylic acids, esters and oxo and oxa compounds is generally not more than 1 wt %. Examples thereof include acetic acid, propionic acid, butyric acid, valeric acid, caproic acid, oxalic acid, malonic acid, succinic acid, 4-hydroxybutyric acid and γ-butyrolactone.

The organic layer containing the carboxylic acid mixture is concentrated. The concentration is generally carried out by distillation. The content of the organic solvent can be reduced to 5 wt % or less, and preferably 1 wt % or less by distillation at a temperature of 10 to 250° C., preferably 20 to 225° C., and more preferably 30 to 200° C. under a pressure of 0.1 to 150 KPa, preferably 0.5 to 110 KPa, and more preferably 2 to 100 KPa.

[Esterification Step]

The carboxylic acid mixture is subjected to an esterification step. The alcohol used for esterification is a linear or branched aliphatic alcohol having 1 to 10 carbon atoms, preferably a linear or branched aliphatic alcohol having 1 to 8 carbon atoms, and more preferably a linear or branched aliphatic alcohol having 1 to 6 carbon atoms. Specific examples of the alcohol include monohydric alcohols such as methanol, ethanol, propanol, butanol, pentanol and hexanol; dihydric alcohols such as 1,6-hexanediol, ethylene glycol, propylene glycol, 1,4-butanediol, 1,5-pentanediol, diethylene glycol, 1,2-diols (e.g. 1,2-ethanediol and 1,2-propanediol) and 1,3-diols (e.g. 1,3-propanediol); and alicyclic alcohols such as cyclohexanol. They may be used alone or in a combination of two or more.

From the viewpoint of simplifying a separation purification process, it is preferable to use 1,6-hexanediol that is the objective compound of the preparation process of the present invention and/or 1,5-pentanediol that is a by-product. 1,5-Pentanediol is useful for the same applications as 1,6-hexanediol. From the viewpoint of separating an excess of the alcohol after the esterification, aliphatic alcohols having 1 to 4 carbon atoms are preferable such as methanol, ethanol, propanol and butanol.

The amount of the alcohol used in the esterification step can be 0.1 to 30 times, advantageously 0.2 to 20 times, and particularly advantageously 0.5 to 10 times the amount of the carboxylic acid mixture subjected to the esterification step (after concentration) on a weight basis.

The esterification can be carried out by bringing the carboxylic acid mixture into contact with the alcohol in a reaction vessel such as a stirring tank, a reaction tube, a bubble column or a distillation column or using a plurality of such reaction vessels as necessary. In the esterification, the generated water is preferably removed from the reaction system. At that time, water can be distilled off together with the alcohol used in excess when the alcohol is a low-boiling alcohol such as methanol, ethanol, propanol or butanol, and water can be distilled off together with an inert gas such as nitrogen when the alcohol is a high-boiling alcohol such as 1,5-pentanediol or 1,6-hexanediol.

Not all carboxyl groups in the system may not be converted to esters of the alcohol used by the esterification. Some of the carboxyl groups may exist in the form of a dimer ester or oligomer ester with an OH-end group of hydroxycaproic acid, for example.

In order to increase the esterification yield, the alcohol and the later-described esterification catalyst can also be added to the reaction solution after the esterification or its distillation bottom residue to make the esterification further proceed in a tank or tube reactor.

The heating temperature in the esterification can be appropriately selected according to the type of the alcohol used, and can be 50 to 400° C., preferably 70 to 300° C., and more preferably 90 to 250° C., for example.

The esterification can be carried out not only under normal pressure but also under reduced pressure conditions or under pressurized conditions, or can be carried out under self-pressure in an esterification apparatus. The esterification is preferably carried out under a pressure of 5 MPa or less, in particular, 2 MPa or less.

The reaction time in the esterification can be appropriately selected according to the type of the alcohol used, the amount of the reaction raw material (carboxylic acid mixture), the catalyst and the like, and can be 0.3 to 20 hours, and preferably 0.5 to 10 hours, for example.

The esterification can be carried out without addition of a catalyst, but can also be carried out in the presence of a catalyst to increase the reaction rate. A homogeneously dissolved catalyst or a solid catalyst can be used as the catalyst. Examples of the homogeneously dissolved catalyst include mineral acids (e.g. sulfuric acid, phosphoric acid and hydrochloric acid), sulfonic acids (e.g. p-toluenesulfonic acid), heteropolyacids (e.g. phosphotungstic acid) and Lewis acids (e.g. aluminum compounds (e.g. aluminum chloride), vanadium compounds, titanium compounds, boron compounds and zinc compounds).

An acidic or hyperacidic material can be used as the solid catalyst. Examples of the material include acidic or hyperacidic metal oxides, for example, metal oxides such as $SiO_2$, $Al_2O_3$, $SnO_2$, $ZrO_2$, layered silicates and zeolite to which a mineral acid residue such as a sulfate group or a phosphate group is added to strengthen the acidity, and organic ion exchangers having a sulfonic acid group or a carboxylic acid group. The solid catalyst can be used in the form of a fixed bed or as a suspended bed.

When the solid catalyst is a suspended bed, the amount of the catalyst used is 0.1 to 5 wt % based on the total amount of the reaction raw material (carboxylic acid mixture) and the alcohol used. When the solid catalyst is a fixed bed, the LHSV (liquid hourly space velocity) is in the range of 0.1 to 5 $h^{-1}$.

The amount of the homogeneously dissolved catalyst or the solid catalyst used is 0.01 to 1 wt % based on the total amount of the reaction raw material (carboxylic acid mixture) and the alcohol used.

When the resulting esterified product is an ester of a low-boiling primary alcohol such as methanol, ethanol, propanol or butanol, the ester can be purified by a conventional method such as distillation.

[Step of Depolymerizing Oligomer Generated in Esterification Step]

The esterified product obtained in the esterification step can be purified by distillation when it is an ester of a low-boiling primary alcohol such as methanol, ethanol, propanol or butanol. Since the bottom liquid contains a large amount of oligomers, it is preferable that the bottom liquid be continuously fed into a tube reactor together with the alcohol used for the esterification, depolymerized to an ester monomer such as dimethyl adipate or methyl 6-hydroxycaproate, purified by distillation or the like, and subjected to the subsequent hydrogenation step.

The depolymerization may be carried out without adding a lower alcohol and a catalyst, but is preferably carried out by adding them.

The catalyst can be a homogeneously dissolved catalyst or a solid catalyst. Examples of the homogeneously dissolved catalyst include mineral acids (e.g. sulfuric acid, phosphoric acid and hydrochloric acid), sulfonic acids (e.g. p-toluenesulfonic acid), heteropolyacids (e.g. phosphotungstic acid), Lewis acids (e.g. aluminum compounds, vanadium compounds, titanium compounds, boron compounds and zinc compounds) and base catalysts (e.g. oxides, carbonates, hydroxides or alkoxides of alkali metal or alkali earth metal, or amines). Lewis acids or base catalysts are preferable, and Lewis acids are more preferable. As Lewis acids, tetraalkoxytitanium, more specifically, tetra-n-butoxytitanium and tetraisopropoxytitanium can be preferably used. In the depolymerization step, water generated by the esterification in the previous step is removed from the system. Therefore, Lewis acid is deactivated with water only slightly and thus can be preferably used. The amount of the homogeneously dissolved catalyst used is generally 0.0001 to 0.5 time, and advantageously 0.001 to 0.3 time the amount of the esterified product obtained in the esterification step (the bottom liquid when the esterified product is purified by distillation) on a weight basis.

An acidic or hyperacidic material can be used as the solid catalyst. Examples of the material include acidic or hyperacidic metal oxides, for example, metal oxides such as $SiO_2$, $Al_2O_3$, $SnO_2$, $ZrO_2$, layered silicates and zeolite to which a mineral acid residue such as a sulfate group or a phosphate group is added to strengthen the acidity, and organic ion exchangers having a sulfonic acid group or a carboxylic acid group. The solid catalyst can be used in the form of a fixed bed or as a suspended bed.

When the homogeneously dissolved acid catalyst is used as a catalyst, the reaction solution after the depolymerization may be neutralized with a base. The amount of the base used can be 1 to 1.5 equivalents per acid equivalent of the catalyst. Examples of the base include oxides, carbonates, hydroxides or alkoxides of alkali metal or alkali earth metal, or amines, generally. They can be used directly or as dissolved in a lower alcohol used for esterification.

The lower alcohol includes an alcohol used for the esterification, for example, a linear or branched aliphatic alcohol having 1 to 10 carbon atoms, and the aliphatic alcohol can be a monohydric or dihydric alcohol. The aliphatic alcohol is preferably a linear or branched aliphatic monohydric alcohol having 1 to 8 carbon atoms (e.g. methanol, ethanol, propanol, isopropanol, n-butanol, isobutanol, n-pentanol or isopentanol), and more preferably methanol. The aliphatic alcohol is also a dihydric alcohol such as butanediol, pentanediol or hexanediol. The amount of the lower alcohol used can be 0.5 to 10 times, and preferably 1 to 5 times the amount of the distillation bottom residue in the previous esterification step containing oligomers on a weight basis.

The depolymerization is generally carried out at high temperature. Specifically, the reaction can be carried out at 50 to 350° C., preferably 200 to 300° C., more preferably 240 to 300° C., and particularly preferably 260 to 280° C. The depolymerization is generally carried out under high pressure. Specifically, the reaction can be carried out under 0.1 to 30 MPa, preferably 1 to 20 MPa, more preferably 5 to 15 MPa, and particularly preferably 10 MPa. Preferably, the depolymerization is carried out at high temperature and under high pressure so that the system is a liquid phase. Since the depolymerization rapidly proceeds at such high temperature and under such high pressure, the reaction time can be 0.5 minute to 1 hour, and preferably 3 to 5 minutes.

[Hydrogenation Step]

The esterified product having undergone the esterification step and optionally the depolymerization step is hydrogenated. The hydrogenation is generally carried out using a catalyst. Any homogeneous or heterogeneous catalysts suitable for hydrogenating carbonyl groups can be used as a catalyst. Examples of the catalyst include metals, metal hydroxides, metallic compounds and mixtures thereof.

Examples of the homogeneous catalysts include those described in Non-Patent Document 2. Examples of the heterogeneous catalysts include those described in Non-Patent Document 3. As metal catalysts, metals of subgroups I and VI to VIII of the Periodic Table described in the aforementioned Non-Patent Documents, in particular, copper, chromium, molybdenum, manganese, rhenium, ruthenium, cobalt, nickel and palladium can be used alone or in a combination of two or more.

In particular, a copper-containing hydrogenation catalyst can be preferably used. Specific examples of such a catalyst include Cu—Cr, Cu—Zn, Cu—Zn—Al, Cu—Zn—Ti, Cu—Fe—Al and Cu—Si. The form of such a catalyst is not particularly limited and may be appropriately selected from forms such as powders, granules and tablets according to the type of the reaction vessel. A copper-zinc catalyst may contain trace aluminum, magnesium, zirconium or the like.

The amount of the catalyst can be appropriately selected depending on the type of the catalyst. Generally, LHSV can be 0.1 to 5 $h^{-1}$ in a gas phase, and the amount can be 0.1 to 5 wt % based on the suspension in a suspended phase.

In the hydrogenation reduction, the heterogeneous catalyst is used in the form of a fixed bed or a suspended bed.

When the hydrogenation is carried out on a fixed bed catalyst in a gas phase, LHSV can be 0.1 to 5 $h^{-1}$ and the pressure can be, for example, 0.1 to 15 MPa, preferably 0.5 to 12 MPa, and more preferably 1 to 10 MPa. The reaction temperature is, for example, 100 to 350° C., and preferably 120 to 300° C.

The hydrogenation can be carried out in a liquid phase under a pressure of 1 to 35 MPa and at a temperature of 100 to 350° C., and preferably under a pressure of 5 to 30 MPa and at a temperature of 150 to 300° C.

The hydrogenation reduction can be carried out in one reaction vessel or in a plurality of reaction vessels serially connected to each other. The hydrogenation reduction may be carried out non-continuously, but is preferably carried out continuously.

The reaction mixture obtained by hydrogenation reduction under the aforementioned conditions comprises 1,6-hexanediol as a main component, and 1,5-pentanediol, 1,2-cyclohexanediol, and small amounts of a mono- or dihydric alcohol having 1 to 7 carbon atoms, a mono- or diester having 1 to 7 carbon atoms, a lactone having 4 to 6 carbon atoms and water as other components.

[First Distillation Step]

A component having a boiling point lower than that of water and the alcohol used in the esterification are separated from the mixture obtained by the hydrogenation.

When a monohydric alcohol such as methanol, ethanol, propanol or butanol is used in the esterification, the mixture obtained by the hydrogenation also contains the monohydric alcohol used in the esterification.

The mixture obtained by the hydrogenation is split into the alcohol used in the esterification and water, which occupy the major part of the low-boiling components, and a stream of material containing 1,6-hexanediol as a main component in addition to 1,5-pentanediol, by a membrane system or advantageously a distillation column, for example.

In this case, the pressure can be 1 to 760 Torr, and preferably 100 to 760 Torr. The column top temperature can be 16 to 66.4° C. The column bottom temperature can be 80 to 240° C. and is preferably adjusted to 80 to 220° C.

The low-boiling stream can also be returned to the esterification step directly. For example, it is possible to separate the alcohol used in the esterification and water in the same apparatus as used for separating the excess alcohol in the esterification step or in a separate distillation apparatus, and return the alcohol to the esterification step directly. The stream may be discarded if it is difficult to recover the alcohol by separation. Examples of the distillation apparatus used here include an evaporator, a batch distillation apparatus, a continuous distillation apparatus and a membrane system.

More particularly, the mixture obtained by the hydrogenation can be fed from the bottom of the distillation column at 108.3 g/Hr and distilled under the conditions of distillate: 31.1 g/Hr, column bottom: 78.6 g/Hr and column bottom average residence time: 25.5 min, for example. The column bottom average residence time can be within 24 Hr, preferably within 5 Hr, and more preferably within 1 Hr. A high column bottom temperature or a long column bottom average residence time is not preferable, because polymerization of ε-caprolactone or 6-hydroxycaproic acid ester with 1,6-hexanediol proceeds to cause a lowering of yield of 1,6-hexanediol.

[Second Distillation Step]

The stream of material containing 1,6-hexanediol as a main component which is obtained in the first distillation step is distilled to separate an EV component having a boiling point higher than that of 1,6-hexanediol. Examples of the EV component having a boiling point higher than that of 1,6-hexanediol include an ester compound of 1,6-hexanediol with 6-hydroxycaproic acid (6-hydroxyhexyl 6-hydroxycaproate), 5-hydroxypentyl 6-hydroxycaproate, 5-hydroxypentyl 5-hydroxyvalerate, 6-hydroxyhexyl 5-hydroxyvalerate, and an ester compound of a 5-hydroxyvaleric acid dimer, a 6-hydroxycaproic acid dimer or the like with 1,6-hexanediol.

Examples of the distillation apparatus used here include a batch distillation apparatus, a continuous distillation apparatus and a membrane system. In this distillation step, the stream of material containing 1,6-hexanediol as a main component which is obtained in the first distillation step can be fed by the middle stage of the aforementioned distillation column (between the concentration part and the recovery part in the distillation column) at 91.1 g/Hr and distilled under a pressure of 1 to 760 Torr, preferably 1 to 100 Torr, and more preferably 1 to 50 Torr at a column bottom temperature of 100 to 250° C., preferably 100 to 220° C., and more preferably 100 to 200° C. for a column bottom average residence time of within 24 Hr, preferably within 16 Hr, and more preferably 10 Hr, for example.

The EV component having a boiling point higher than that of 1,6-hexanediol which is separated in the second distillation step does not need to be subjected to a saponification step by addition of alkali. Therefore, the bottom liquid is not turbid but transparent and has a good viscosity, and can be returned to the hydrogenation step as is. By returning the high-boiling EV component to the hydrogenation step as is, 1,6-hexanediol and an effective component that is a raw material thereof are recovered, making it possible to increase the yield ([high-boiling EV component recovery step]).

[Third Distillation Step]

The product containing 1,6-hexanediol as a main component which is obtained by separating the high-boiling component in the second distillation step is distilled to separate an EV component having a boiling point lower than that of 1,6-hexanediol. Examples of the EV component having a boiling point lower than that of 1,6-hexanediol include δ-valerolactone, 5-hydroxyvaleric acid ester, ε-caprolactone and 6-hydroxycaproic acid ester. Trace amounts of the low-boiling alcohol and water that cannot be separated in the first distillation step may be separated in this step.

Examples of the distillation apparatus used here include a batch distillation apparatus, a continuous distillation apparatus and a membrane system. In the third distillation step, the product containing 1,6-hexanediol which is obtained in the second distillation step can be fed by the middle stage of the aforementioned distillation column (between the concentration part and the recovery part in the distillation column) at 119.8 g/Hr and distilled under a pressure of 1 to 760 Torr, preferably 1 to 100 Torr, and more preferably 1 to 50 Torr at a column bottom temperature of 100 to 250° C., preferably 100 to 220° C., and more preferably 100 to 200° C. for a column bottom average residence time of within 10 Hr, preferably within 5 Hr, and more preferably within 2 Hr, for example. Here, distillation can be carried out at an ester value (EV) of the bottom liquid of 4.2 mg KOH/g or less, preferably 2 mg KOH/g or less, and more preferably 1 mg KOH/g or less. Here, the ester value of the bottom liquid refers to a content of a lactone such as δ-valerolactone or ε-caprolactone, 5-hydroxyvaleric acid ester, 6-hydroxycaproic acid ester, a dimer ester of 6-hydroxycaproic acid ester with 1,5-pentanediol or 1,6-hexanediol, or the like.

In the present invention, the second distillation step and the third distillation step are carried out in this order. For example, if the distillation steps are carried out in the reverse order, ε-caprolactone is generated by terminal cyclization and elimination of the high-boiling EV component (e.g. 6-hydroxyhexyl 6-hydroxycaproate) when 1,6-hexanediol and the high-boiling component are separated in the second distillation step after the third distillation step, and thus ε-caprolactone is included in the fourth distillation step, making it difficult to obtain high-quality 1,6-hexanediol in a high yield.

[Fourth Distillation Step]

Further, the product containing 1,6-hexanediol which is obtained in the third distillation step is distilled and purified to obtain high-quality 1,6-hexanediol.

Examples of the distillation apparatus used here include a batch distillation apparatus, a continuous distillation apparatus and a membrane system. In batch distillation, a low-boiling fraction such as ε-caprolactone or 6-hydroxy-caproic acid ester can be distilled off as an initial fraction, a fraction containing 1,5-pentanediol as a main component can be obtained as a medium fraction, and 1,6-hexanediol can be obtained as a main fraction; however, polymerization tends to occur in the bottom liquid and the recycled amount tends to be increased. Accordingly, in continuous distillation, it is preferable to obtain 1,5-pentanediol from the column top and distill off and obtain 1,6-hexanediol from the middle (side stream part) of the recovery part (packing part between the feed liquid port and the bottom liquid in the distillation column).

In the fourth distillation step, the product containing 1,6-hexanediol which is obtained in the third distillation step can be distilled using the aforementioned distillation column under a pressure of 1 to 760 Torr, preferably 1 to 100 Torr, and more preferably 1 to 50 Torr at a column bottom temperature of 100 to 250° C., preferably 100 to 220° C., and more preferably 100 to 200° C. for a column bottom average residence time of within 24 Hr, preferably within 16 Hr, and more preferably within 10 Hr, for example.

1,6-Hexanediol obtained by the aforementioned preparation process has an ester value (EV) of 1 mg KOH/g or less, preferably 0.5 mg KOH/g or less, and more preferably 0.1 mg KOH/g or less.

EXAMPLES

The present invention will be described more specifically with reference to examples below; however, the scope of the present invention is not limited thereto.

The distillation yield was calculated from the yield obtained by distillation based on 1,6-hexanediol obtained in the hydrogenation step.

The ester value (EV) of the product of the hydrogenation step was determined as equal to the saponification value (SV), since the product had an acid value (AV) nearly equal to 0.

The saponification value was a weight (mg) of KOH (potassium hydroxide) necessary for saponifying a sample unit amount (1 g) and was determined by neutralization titration (back titration) of the excess KOH after saponification with hydrochloric acid.

Example 1

Step 1: Oxidation of Cyclohexane and Extraction with Water

Cyclohexane was oxidized with molecular oxygen in the presence of a cobalt catalyst (cobalt octylate) under the conditions of 160° C. and 1 MPa, followed by extraction with water under the conditions of 160° C. and 1 MPa to obtain a carboxylic acid mixture (aqueous extract) having the following composition.

Aqueous extract of cyclohexane oxide
(Composition of aqueous extract)
Valeric acid: 0.1 wt %
5-Hydroxyvaleric acid: 0.11 wt %

Caproic acid: 0.02 wt %
Succinic acid: 0.3 wt %
5-Hydroxycaproic acid: 3.8 wt %
Glutaric acid: 0.3 wt %
Adipic acid: 2.4 wt %
1,2-Cyclohexanediol: 0.02 wt %
1,4-Cyclohexanediol: 0.04 wt %
Others: Water and trace components Step 2: Concentration of Aqueous Extract Then, the extract was concentrated under the condition of 13 KPa to obtain a concentrate having the following composition.
(Composition)
6-Hydroxycaproic acid: 27.9 wt % (about 90 wt % of which was oligomers)
Adipic acid: 19.8 wt % (about 50 wt % of which was oligomers)
$H_2O$: 2.0 wt %
1,4-Cyclohexanediol: 0.7 wt %

Step 3: Esterification

Figure 1:
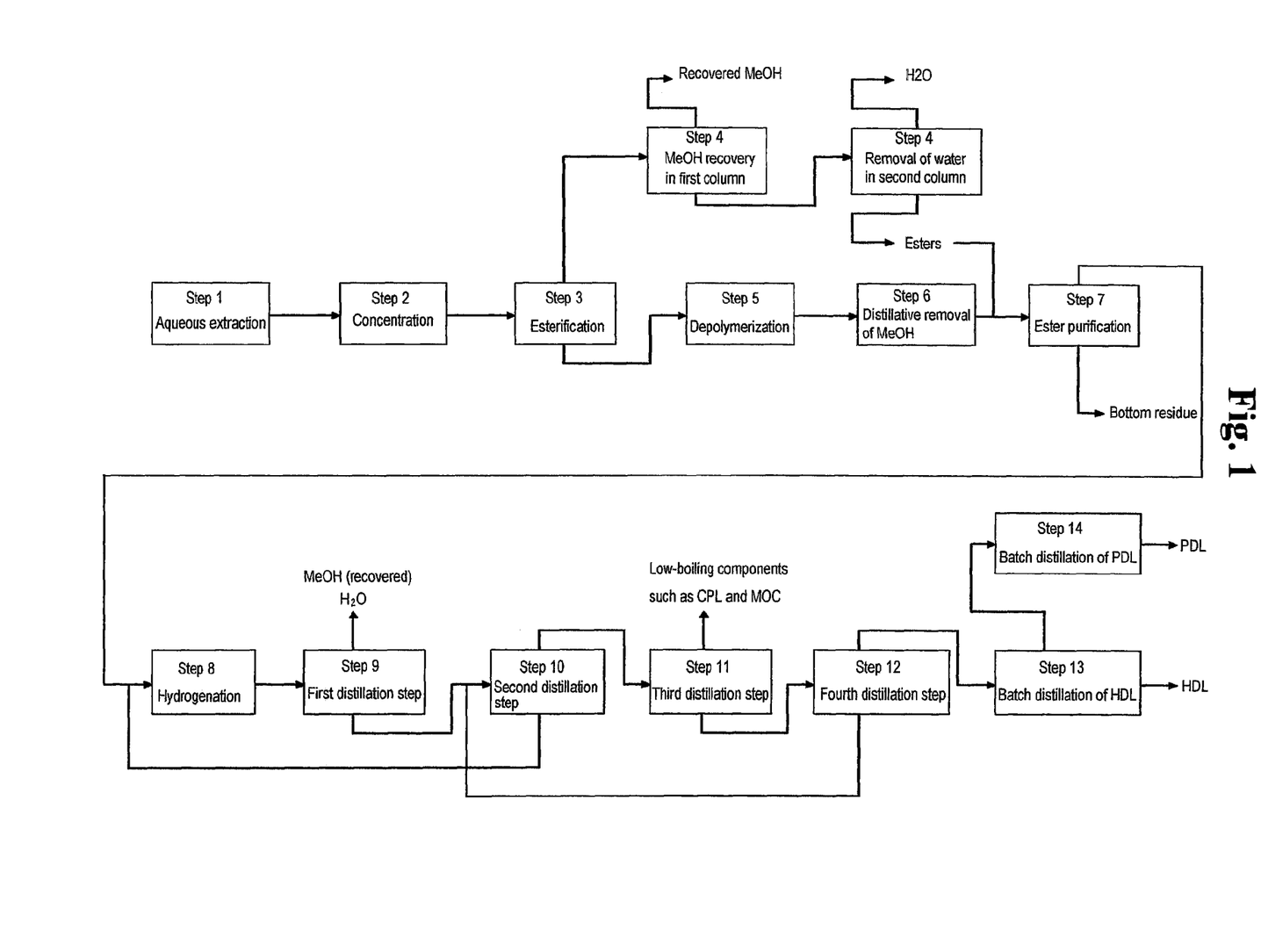
FIG. 1 shows a flow chart of Example 1, where CPL represents ε-caprolactone, MOC represents methyl 6-hydroxycaproate, PDL represents 1,5-pentanediol, and HDL represents 1,6-hexanediol.
Figure 2:
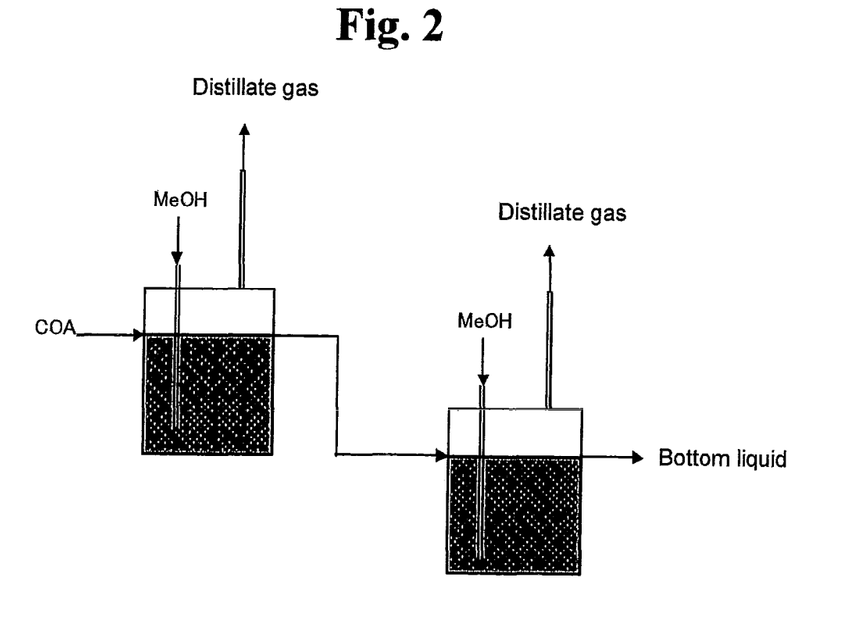
FIG. 2 shows a drawing of an apparatus in the esterification step of Example 1, where COA represents a carboxylic acid mixture.

The bottom liquid (aforementioned concentrate) obtained in Step 2 was continuously fed into a reaction apparatus (700 cc gas-liquid reaction tank×2, see FIG. 2) at 700 g/h and methanol was gasified. Thereafter, the reaction solution was bubbled with methanol in the two tanks at 350 g/h, respectively. At that time, the temperature in the reaction tanks was maintained at 240° C. by external heating, and the pressure was adjusted with a back pressure regulating valve so as to keep the distillate gas at 1 MPa. As a result, a distillate gas and a bottom liquid were respectively obtained as indicated below.
  Distillate gas (after cooling and condensation): 757 g/h
  $H_2O$: 6.9 wt %
  Dimethyl adipate: 5.2 wt %
  Methyl hydroxycaproate: 0.9 wt %
  1,4-Cyclohexanediol: Trace amount
  Adipic acid: Trace amount
  6-Hydroxycaproic acid: Trace amount
  Others: MeOH, low-boiling components, etc.
  Bottom liquid: 643 g/h
  Acid value: 20 mg KOH/g
  $H_2O$: 0.1 wt %
  Others: Oligomer components such as adipic acid and hydroxycaproic acid, etc.

Step 4: Recovery of Methanol and Distillative Removal of Water

The distillate gas obtained above was cooled and condensed. Then, methanol was recovered in a first distillation column and $H_2O$ and a low-boiling fraction were removed in a second distillation column under the following conditions.
  First Distillation Column
  Distillation apparatus: Sulzer Labo Packing EX (Sumitomo Heavy Industries), 5 units
  Distillation conditions: 0.1 kg/cm$^2$G, column top: 66° C., column bottom: 111° C.
  Second Distillation Column
  Distillation apparatus: Sulzer Labo Packing EX (Sumitomo Heavy Industries), 5 units
  Distillation conditions: 410 Torr, column top: 76° C., column bottom: 190° C.

As a result, a concentrate having the following composition was obtained.
MeOH: 0.2 wt %
Dimethyl adipate: 72.3 wt %
Methyl hydroxycaproate: 17.5 wt %
$H_2O$: 0.1 wt %
Caprolactone: 0.8 wt %
1,4-Cyclohexanediol (cis+trans): N.D.
Dimethyl glutarate: 3.7 wt %
Dimethyl succinate: 1.2 wt %
Others (mainly components having a boiling point lower than that of dimethyl adipate): 4.2 wt %

Step 5: Depolymerization

The bottom liquid obtained in Step 3 at 100 g/h, methanol at 200 g/h and a tetrabutoxytitanium catalyst at 0.1 g/h were continuously fed into a tube reactor, and depolymerization was carried out under the following conditions.
  Reactor conditions: 270° C., 10 MPa, residence time: 5 minutes Step 6: Removal of Methanol The reaction solution obtained by the depolymerization in Step 5 was distilled under the following conditions to remove methanol and a low-boiling fraction.
  Distillation apparatus: Sulzer Labo Packing (5 units)
  Distillation conditions: 160 Torr, column top: 34° C., column bottom: 89° C.

Step 7: Purification of Ester

The bottom liquids obtained in Steps 4 and 6 were distilled under the following conditions to obtain dimethyl adipate, methyl 6-hydroxycaproate and the like.
  Distillation apparatus: Sulzer Labo Packing (27 units)
  Distillation conditions: 5 Torr, column top: 105° C., column bottom: 190° C.
  The column bottom liquid (bottom residue) by ester purification of Step 7 contains an effective component of 1,6-hexanediol, and therefore can be recovered by recycling to Step 5.

Step 8 Hydrogenation

The ester obtained in Step 7 was hydrogenated in a solid-liquid reaction tank under the following conditions.
  Hydrogenation apparatus: Suspended bed
  Hydrogenation conditions: 250° C., 25 MPa, catalyst: CuO—ZnO catalyst: 1 wt %, 5 hr
  Result: Saponification value conversion rate: 98%

Step 9: First Distillation Step

The mixture obtained by the hydrogenation was distilled to separate water and a low-boiling component.
  Distillation apparatus: Sulzer Labo Packing EX (Sumitomo Heavy Industries), 20 units
  Distillation conditions: Normal pressure, column top: 66.4° C., column bottom 191° C.
(Composition of Mixture Obtained by Hydrogenation)
$H_2O$: 0.74 wt %
MeOH: 27.35 wt %
1-Hexanol: 0.16 wt %
Dimethyl adipate: 0.12 wt %
ε-Caprolactone: 0.04 wt %

1,4-Butanediol: 0.73 wt %
Methyl 6-hydroxycaproate: 1.88 wt %
1,5-Pentanediol: 6.28 wt %
1,4-Cyclohexanediol (cis+trans): 0.14 wt %
1,6-Hexanediol: 53.97 wt %
Others (mainly high-boiling substances including an ester of 1,6-hexanediol with 6-hydroxycaproic acid): 8.59 wt %
Saponification value: 18.63 mg KOH/g The column top liquid and the column bottom liquid of this distillation step had the following compositions, respectively.
(Composition of Column Top Liquid)
$H_2O$: 1.95 wt %
MeOH: 93.9 wt %
(Composition of column bottom liquid (bottom residue))
$H_2O$: 0.3 wt %
MeOH: 2.2 wt %
1-Hexanol: 0.17 wt %
δ-Valerolactone: 0.02 wt %
Dimethyl adipate: 0.04 wt %
ε-Caprolactone: 0.09 wt %
1,4-Butanediol: 1.12 wt %
Methyl 6-hydroxycaproate: 2.49 wt %
1,5-Pentanediol: 8.22 wt %
1,4-Cyclohexanediol (cis+trans): 0.23 wt %
1,6-Hexanediol: 76.09 wt %
Others (mainly high-boiling substances including an ester of 1,6-hexanediol with 6-hydroxycaproic acid): 9.03 wt %
Saponification value: 25.9 mg KOH/g
(Distillation Conditions)
Feed (column bottom): 108.3 g/Hr
Distillate: 31.1 g/Hr
Column bottom: 78.6 g/Hr
Column bottom average residence time: 25.5 min

Step 10: Second Distillation Step

The column bottom liquid (bottom residue) obtained in the first distillation step was distilled under the following conditions to separate crude 1,6-hexanediol and a high-boiling compound.
Distillation Apparatus:
Concentration part: Sulzer Labo Packing EX (Sumitomo Heavy Industries), 10 units
Recovery part: Sulzer Labo Packing EX (Sumitomo Heavy Industries), 6 units
Distillation conditions: pressure: 10 Ton, column top: 140° C., column bottom: 157° C., feed stage: 146° C.
(Composition of Crude 1,6-Hexanediol)
$H_2O$: 0.3 wt %
MeOH: 2.2 wt %
1-Hexanol: 0.17 wt %
δ-Valerolactone: 0.02 wt %
Dimethyl adipate: 0.04 wt %
ε-Caprolactone: 0.09 wt %
1,4-Butanediol: 1.12 wt %
Methyl 6-hydroxycaproate: 2.49 wt %
1,5-Pentanediol: 8.22 wt %
1,4-Cyclohexanediol (cis+trans): 0.23 wt %
1,6-Hexanediol: 76.09 wt %
Others (mainly high-boiling substances including an ester of 1,6-hexanediol with 6-hydroxycaproic acid): 9.03 wt %
Saponification value: 25.9 mg KOH/g The column top liquid and the column bottom liquid of this distillation step had the following compositions, respectively.
(Composition of Column Top Liquid)
$H_2O$: 0.3 wt %
MeOH: 0.07 wt %
1-Hexanol: 0.15 wt %
δ-Valerolactone: 0.09 wt %
Dimethyl adipate: 0.08 wt %
ε-Caprolactone: 3.08 wt %
1,4-Butanediol: 1.3 wt %
Methyl 6-hydroxycaproate: 2.38 wt %
1,5-Pentanediol: 9.17 wt %
1,4-Cyclohexanediol (cis+trans): 0.26 wt %
1,6-Hexanediol: 81.02 wt %
Others (mainly low-boiling substances): 2.1 wt %
Saponification value: 26.2 mg KOH/g
(Composition of Column Bottom Liquid)
$H_2O$: 0.2 wt %
δ-Valerolactone: 0.05 wt %
ε-Caprolactone: 1.28 wt %
1,5-Pentanediol: 0.28 wt %
1,4-Cyclohexanediol (cis+trans): 0.1 wt %
1,6-Hexanediol: 61.5 wt %
Others (mainly high-boiling substances including an ester of 1,6-hexanediol with 6-hydroxycaproic acid): 36.59 wt %
Saponification value: 82.8 mg KOH/g
(Distillation Conditions)
Feed (middle stage: between concentration part and recovery part): 91.1 g/Hr
Distillate: 80.8 g/Hr
Column bottom: 9.5 g/Hr
Column bottom main residence time: 5 Hr The column bottom liquid has a low viscosity because caustic soda is not added. Therefore, the column bottom liquid can be recycled to the hydrogenation step.

Step 11: Third Distillation Step

The column top liquid obtained in the second distillation step was distilled under the following conditions to separate ε-caprolactone and 6-hydroxycaproic acid ester.
Distillation Apparatus:
Concentration part: Sulzer Labo Packing EX (Sumitomo Heavy Industries), 10 units
Recovery part: Sulzer Labo Packing EX (Sumitomo Heavy Industries), 6 units
Distillation conditions: pressure: 30 Torr, column top: 137° C., column bottom: 169° C., feed stage: 159° C.
(Composition of Crude 1,6-Hexanediol)
$H_2O$: 0.3 wt %
MeOH: 0.07 wt %
1-Hexanol: 0.15 wt %
δ-Valerolactone: 0.09 wt %
Dimethyl adipate: 0.08 wt %
ε-Caprolactone: 3.08 wt %
1,4-Butanediol: 1.3 wt %
Methyl 6-hydroxycaproate: 2.38 wt %
1,5-Pentanediol: 9.17 wt %
1,4-Cyclohexanediol (cis+trans): 0.26 wt %
1,6-Hexanediol: 81.02 wt %
Others (mainly low-boiling substances): 2.1 wt %
Saponification value: 26.2 mg KOH/g The column top liquid and the column bottom liquid of this distillation step had the following compositions, respectively.
(Composition of Column Top Liquid)
$H_2O$: 0.2 wt %
MeOH: 0.04 wt %
1-Hexanol: 1.1 wt %
δ-Valerolactone: 0.8 wt %
Dimethyl adipate: 0.68 wt %
ε-Caprolactone: 27.0 wt %
1,4-Butanediol: 13.2 wt %

Methyl 6-hydroxycaproate: 24.2 wt %
1,5-Pentanediol: 4.3 wt %
Saponification value: 243.6 mg KOH/g
(Composition of Column Bottom Liquid)
$H_2O$: 0.2 wt %
ε-Caprolactone: 0.01 wt %
1,4-Butanediol: 0.02 wt %
Methyl 6-hydroxycaproate: 0.03 wt %
1,5-Pentanediol: 8.12 wt %
1,4-Cyclohexanediol (cis+trans): 0.28 wt %
1,6-Hexanediol: 90.62 wt %
Others (unknown components): 0.7 wt %
Saponification value: 0.4 mg KOH/g
(Distillation Conditions)
Feed (middle stage: between concentration part and recovery part): 119.8 g/Hr
Distillate: 14.9 g/Hr
Column bottom: 103.2 g/Hr
Column bottom main residence time: 39 min

Step 12: Fourth Distillation Step

The column bottom liquid obtained in the third distillation step was distilled under the following conditions to obtain 1,5-pentanediol and 1,6-hexanediol fractions.
Distillation Apparatus:
Concentration part: Sulzer Labo Packing EX (Sumitomo Heavy Industries), 10 units
Recovery part: Sulzer Labo Packing EX (Sumitomo Heavy Industries), 6 units
Distillation conditions: pressure: 50 Torr, column top: 174° C., column bottom: 179° C., feed stage: 175° C.
(Feed Liquid (Column Bottom Liquid Obtained in Third Distillation Step))
$H_2O$: 0.2 wt %
ε-Caprolactone: 0.01 wt %
1,4-Butanediol: 0.02 wt %
Methyl 6-hydroxycaproate: 0.03 wt %
1,5-Pentanediol: 8.12 wt %
1,4-Cyclohexanediol (cis+trans): 0.28 wt %
1,6-Hexanediol: 90.62 wt %
Others (unknown components): 0.7 wt %
Saponification value: 0.4 mg KOH/g
The column top liquid and the column bottom liquid of this distillation step had the following compositions, respectively.
(Composition of Column Top Liquid)
δ-Valerolactone: 0.01 wt %
ε-Caprolactone: 0.06 wt %
Methyl 6-hydroxycaproate: 0.07 wt %
1,5-Pentanediol: 8.42 wt %
1,4-Cyclohexanediol (cis+trans): 0.3 wt %
1,6-Hexanediol: 91.0 wt %
Others (unknown components): 0.14 wt %
Saponification value: 0.53 mg KOH/g
(Composition of Column Bottom Liquid)
δ-Valerolactone: 0.01 wt %
ε-Caprolactone: 0.05 wt %
Methyl 6-hydroxycaproate: 0.01 wt %
1,5-Pentanediol: 0.22 wt %
1,4-Cyclohexanediol (cis+trans): 0.2 wt %
1,6-Hexanediol: 94.8 wt %
Others (mainly high-boiling components): 4.71 wt %
Saponification value: 5.03 mg KOH/g
Feed (middle stage: between concentration part and recovery part): 103.9 g/Hr
Distillate: 98.1 g/Hr
Column bottom: 7.8 g/Hr
Column bottom main residence time: 388 min
The column bottom liquid can be recycled to the second distillation step or the hydrogenation step.

Step 13: Rectification of 1,6-Hexanediol and Acquisition of 1,6-Hexanediol

Distillation apparatus: Sulzer Labo Packing EX (Sumitomo Heavy Industries), 17 units
A 1 L flask was charged with about 710.4 g of the distillate of the fourth distillation step. Next, 264.2 g of a low-boiling substance was distilled off at a reduced pressure of 5 Torr at a reflux ratio of 30, and 380.5 g of a main fraction containing 1,6-hexanediol as a main component and 42.3 g of a column bottom liquid were further obtained at a reflux ratio of 5.

The main fraction was 1,6-hexanediol having a gas chromatographic purity of 99.8% or higher and contained 0.1% or less of impurity EV components (δ-valerolactone, ε-caprolactone, methyl 6-hydroxycaproate). The saponification value was 0.5 mg KOH/g or less (saponification value (SV) =ester value (EV)+acid value (AV); however, in the present invention, saponification value (SV)=ester value (EV) because AV is nearly equal to 0).

Step 14: Rectification of 1,5-Pentanediol and Acquisition of 1,5-Pentanediol Distillation apparatus: Sulzer Labo Packing EX (Sumitomo Heavy Industries), 16 units
A 1 L flask was charged with 1560.7 g of the initial fraction of the low-boiling substance obtained by the aforementioned rectification of 1,6-hexanediol. Next, 385.6 g of a low-boiling substance was distilled off at a reduced pressure of 36 Torr at a reflux ratio of 15, and 604.5 g of a main fraction containing 1,5-pentanediol as a main component and 570.3 g of a column bottom liquid were obtained.

The main fraction was 1,5-pentanediol having a gas chromatographic purity of 99.8% or higher and contained 0.1 wt % or less of impurity EV components (δ-valerolactone, ε-caprolactone, methyl 6-hydroxycaproate). The saponification value was 0.1 mg KOH/g (saponification value (SV)=ester value (EV)+acid value (AV); however, in the present invention, saponification value (SV)=ester value (EV) because AV is nearly equal to 0).

1,6-Hexanediol distillation yield: 71% (without recycling)
The column bottom liquid of the second distillation step (8.5%), the column bottom liquid of the fourth distillation step (7.3%), and the column bottom liquid during rectification of 1,6-hexanediol (5.7%) can be recovered by recycling.
1,6-Hexanediol distillation yield: 90% (with recycling)

Comparative Example 1

$H_2O$ and MeOH were distilled off from the same hydrogenated liquid as in Example 1 using an evaporator at 100 Torr at a bath temperature of 80° C., followed by concentration; the resulting liquid was used.
Distillation apparatus: Sulzer Labo Packing EX (Sumitomo Heavy Industries), 10 units
A 1 L flask was charged with 750.4 g of the hydrogenated liquid. Next, 226.8 g of a low-boiling substance was distilled off at a reduced pressure of 10 Torr at a reflux ratio of 3, and 306.9 g of a main fraction containing 1,6-hexanediol as a main component, 112.1 g of a final distillate and 106.2 g of a column bottom liquid were obtained.
(Composition of Main Fraction)
Dimethyl adipate: 0.24 wt %

ε-Caprolactone: 0.85 wt %
Methyl 6-hydroxycaproate: 1.61 wt %
1,5-Pentanediol: 14.1 wt %
1,6-Hexanediol: 73.4 wt %
Others: 9.8 wt %
Saponification value: 13.28 mg KOH/g The main fraction was distilled again under the following conditions.

Distillation apparatus: Sulzer Labo Packing EX (Sumitomo Heavy Industries), 20 units A 500 mL flask was charged with 306.9 g of the main fraction. Next, 160.3 g of a low-boiling substance was distilled off at a reduced pressure of 10 Torr at a reflux ratio of 5, and 41.0 g of a main fraction containing 1,6-hexanediol as a main component, 70.4 g of a final distillate and 27.4 g of a bottom residue were obtained.

The main fraction was 1,5-pentanediol having a gas chromatographic purity of 99.8% or higher and contained 0.1 wt % or less of impurity EV components (δ-valerolactone, ε-caprolactone, methyl 6-hydroxycaproate). The saponification value was 0.49 mg KOH/g.

In the final distillate, ε-caprolactone was generated by terminal cyclization and elimination of the high-boiling component and was entrained in the 1,6-hexanediol distillate, resulting in a lowering purity of 1,6-hexanediol. The saponification value was 2.9 mg KOH/g.

1,6-hexanediol distillation yield: 7.6% (without recycling)

Comparative Example 2

Water and methanol were distilled off from the same hydrogenated liquid as in Example 1 using an evaporator at a pressure of 100 Torr at a bath temperature of 80° C., followed by concentration; the resulting liquid was used.

Distillation apparatus: Sulzer Labo Packing EX (Sumitomo Heavy Industries), 10 units A 1 L flask was charged with 519.0 g of the hydrogenated liquid. Next, 45.1 g of a low-boiling substance was distilled off under a reduced pressure of 10 Torr at a reflux ratio of 5, and 364.7 g of a main fraction containing 1,6-hexanediol as a main component, 48.2 g of a final distillate and 53.1 g of a column bottom liquid were obtained.
(Composition of Main Fraction)
Dimethyl adipate: 0.13 wt %
ε-Caprolactone: 1.91 wt %
Methyl 6-hydroxycaproate: 2.11 wt %
1,5-Pentanediol: 13.81 wt %
1,6-Hexanediol: 74.54 wt %
Others: 7.5 wt %
Saponification value: 22.14 mg KOH/g The main fraction was distilled again under the following conditions.

Distillation apparatus: Sulzer Labo Packing EX (Sumitomo Heavy Industries), 20 units A 500 mL flask was charged with 315.0 g of the main distillate. Caustic soda was added under a reduced pressure of 10 Torr so that Na/saponification value (main distillate) was 1.2 (molar ratio), and saponification was carried out by refluxing for one hour. Thereafter, 124.9 g of a low-boiling substance was distilled off at a reflux ratio of 5, and 94.4 g of a main fraction containing 1,6-hexanediol as a main component and 83.5 g of a bottom residue were obtained.

The main fraction had an EV of 0.37 mg KOH/g.

Because the EV component was saponified by adding caustic soda before distillation, ε-caprolactone derived from terminal cyclization and elimination of a high-boiling ester was not generated and entrained in the main 1,6-hexanediol fraction; however, the bottom residue was viscous and turbid. This bottom residue contained 77.5 wt % of 1,6-hexanediol but could not be returned to the hydrogenation step, resulting in an increased loss of 1,6-hexanediol.

1,6-Hexanediol distillation yield: 32.5% (without recycling)

Comparative Example 3

The carboxylic acid mixture (COA) described in Example 1 was esterified with a hydrogenated liquid containing 1,6-hexanediol as a main component, followed by hydrogenation of the carboxylic acid ester; the resulting liquid was used as a raw material.

Distillation apparatus: Sulzer Labo Packing EX (Sumitomo Heavy Industries), 10 units A 1 L flask was charged with 595.0 g of the hydrogenated liquid. Next, 265.8 g of a low-boiling substance was distilled off under a reduced pressure of 10 Torr at a reflux ratio of 3, and 85.5 g of a main fraction containing 1,6-hexanediol as a main component, 79.3 g of a final distillate and 140.6 g of a column bottom liquid were obtained.

In the final distillate, lactones such as δ-valerolactone and ε-caprolactone were generated by terminal cyclization and elimination of the high-boiling component and were entrained in the 1,6-hexanediol distillate, resulting in a lowering of purity of 1,6-hexanediol. The saponification value was 34.5 mg KOH/g.
(Composition of Main Fraction)
δ-Valerolactone: 0.32 wt %
ε-Caprolactone: 0.18 wt %
1,4-Cyclohexanediol (cis+trans): 1.38 wt %
1,5-Pentanediol: 1.66 wt %
1,6-Hexanediol: 96.0 wt %
Others: 0.46 wt %
Saponification value: 3.70 mg KOH/g The main fraction was distilled again under the following conditions.

Distillation apparatus: Spinning band distillation apparatus (number of theoretical plates: 25, 2000 rpm)

A 100 mL flask was charged with 85.5 g of the main distillate. Next, 32.4 g of a low-boiling substance was distilled off at a reduced pressure of 10 Torr at a reflux ratio of 5, and 45.9 g of a main fraction containing 1,6-hexanediol as a main component and 83.5 g of a bottom residue were obtained.

The main fraction had an EV of 0.45 mg KOH/g.

1,6-Hexanediol distillation yield: 14.0% (without recycling)

INDUSTRIAL APPLICABILITY

The preparation process of the present invention can produce 1,6-hexanediol having a significantly reduced ester value (EV) in a high yield and is highly industrially advantageous.

The invention claimed is:

1. A process for preparing 1,6-hexanediol from a carboxylic acid mixture containing adipic acid and 6-hydroxycaproic acid, wherein the carboxylic acid mixture is obtained as a by-product in oxidization of cyclohexane to cyclohexanone/cyclohexanol using oxygen or an oxygen-containing gas, the process comprises esterifying these acids with a lower alcohol, followed by hydrogenation, and the process is characterized by comprising the following steps of:
   a) separating a component having a boiling point lower than that of water and the alcohol used in the esterification from a mixture obtained by the hydrogenation in a first distillation step;

b) separating an EV component having a boiling point higher than that of 1,6-hexanediol further in a second distillation step;
c) separating an EV component having a boiling point lower than that of 1,6-hexanediol further in a third distillation step; and then
d) obtaining 1,6-hexanediol in a fourth distillation step, in this order wherein 1,6-hexanediol has an ester value of 1 mg KOH/g or less.

2. The preparation process according to claim 1, wherein the mixture obtained by the hydrogenation which is then subjected to the first distillation step a) is obtained by
1) oxidizing cyclohexane to cyclohexanone/cyclohexanol using oxygen or an oxygen-containing gas and obtaining a carboxylic acid mixture containing adipic acid and 6-hydroxycaproic acid by extraction of a reaction mixture with water;
2) treating the carboxylic acid mixture with an aliphatic alcohol having 1 to 4 carbon atoms to esterify mono- and dicarboxylic acids in the carboxylic acid mixture to obtain a mixture containing carboxylic acid esters;
3) separating a component having a boiling point lower than that of water and an excess of the alcohol from the mixture containing carboxylic acid esters by distillation;
4) distilling a bottom liquid after the separation by distillation to separate the carboxylic acid esters; and then
5) hydrogenating the resulting carboxylic acid esters.

3. The process for preparing 1,6-hexanediol according to claim 1, wherein the EV component having a boiling point higher than that of 1,6-hexanediol, which is separated in the second distillation step, is hydrogenated and introduced into the first distillation step.

4. The process for preparing 1,6-hexanediol according to claim 2, wherein the EV component having a boiling point higher than that of 1,6-hexanediol, which is separated in the second distillation step, is hydrogenated and introduced into the first distillation step.

* * * * *